(12) United States Patent
Maier et al.

(10) Patent No.: US 6,667,276 B1
(45) Date of Patent: Dec. 23, 2003

(54) SURFACTANT SYSTEMS FOR LIQUID AQUEOUS PREPARATIONS

(75) Inventors: Thomas Maier, Hofheim (DE); Jochen Würtz, Bad Kreuznach (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/198,725

(22) Filed: Nov. 24, 1998

(30) Foreign Application Priority Data

Nov. 27, 1997 (DE) .......................................... 197 52 552

(51) Int. Cl.⁷ .......................... A01N 25/30; A01N 57/02
(52) U.S. Cl. ...................... 504/127; 504/128; 504/206; 504/365; 514/975
(58) Field of Search ................................ 504/127, 128, 504/206, 365; 514/975

(56) References Cited

U.S. PATENT DOCUMENTS

| | | |
|---|---|---|
| 5,227,402 A | 7/1993 | Röchling et al. ............ 514/521 |
| 5,298,529 A | 3/1994 | Narayanan ................... 514/788 |
| 5,300,529 A | 4/1994 | Narayanan ................... 514/788 |
| 5,317,042 A | 5/1994 | Narayanan ................... 514/772 |
| 5,324,708 A | 6/1994 | Moreno et al. .............. 504/206 |
| 5,326,789 A | 7/1994 | Narayanan ................... 514/788 |
| 5,334,585 A | 8/1994 | Derian et al. .................. 514/74 |
| 5,369,082 A | 11/1994 | Frisch et al. ................. 504/127 |
| 5,565,409 A | 10/1996 | Sato et al. ................... 504/127 |
| 6,030,923 A * | 2/2000 | Okano et al. ................ 504/116 |

FOREIGN PATENT DOCUMENTS

| | | |
|---|---|---|
| CA | 1209361 | 8/1986 |
| DE | 32 35 612 | 3/1984 |
| DE | 41 16 516 | 11/1991 |
| EP | 0006348 | 1/1980 |
| EP | 0143547 | 6/1985 |
| EP | 0160182 | 11/1985 |
| EP | 0290416 | 11/1988 |
| EP | 0394211 | 10/1990 |
| EP | 0432062 | 6/1991 |
| EP | 0448538 | 9/1991 |
| EP | 0472310 | 2/1992 |
| EP | 0500401 | 6/1992 |
| EP | 0499587 | 8/1992 |
| EP | 0617894 | 10/1994 |
| EP | 0648414 | 4/1995 |
| GB | 2049427 | 12/1980 |
| GB | 2157952 | 11/1985 |
| GB | 2267825 | 12/1993 |
| JP | 7-89817 | 4/1995 |
| WO | WO 84/03607 | 9/1984 |
| WO | WO 90/06681 | 6/1990 |
| WO | WO 90/07277 | 7/1990 |
| WO | WO 92/13454 | 8/1992 |
| WO | WO 93/14630 | 8/1993 |
| WO | WO 96/08150 | 3/1996 |
| ZA | 0499587 | 1/1992 |

OTHER PUBLICATIONS

Derwent Abstract of DE 4029304 which relates to EP 0,476,555 which is not enclosed.

* cited by examiner

Primary Examiner—S. Mark Clardy
(74) Attorney, Agent, or Firm—Frommer Lawrence & Haug LLP

(57) ABSTRACT

The invention relates to surfactant systems for liquid aqueous or aqueous-organic formulations comprising a mixture of one or more basic cosurfactants and one or more surfactants from the group of the acidic phosphoric esters. The surfactant system makes possible the preparation of stable liquid formulations for active compounds, the formulations comprising (a) one or more water-soluble active compounds (type (a)) and (b) optionally one or more water-insoluble active compounds (type (b)), (c) optionally organic solvents, (d) the abovementioned surfactant system and water.

The formulations are either single-phase aqueous or aqueous-organic formulations of type-(a) active compounds, for example glufosinate-ammonium or glyphosate(salts), or they are microemulsions of type-(a) and type-(b) active compounds, for example diphenyl ether herbicides.

16 Claims, No Drawings

SURFACTANT SYSTEMS FOR LIQUID AQUEOUS PREPARATIONS

The invention relates to the technical field of surfactant systems for liquid aqueous or aqueous-organic formulations (preparations), preferably comprising an organic and an aqueous phase in the form of a microemulsion. The invention preferably relates to surfactant systems for single-phase or multi-phase formulations of one or more active compounds, where at least one of the active compounds is readily soluble in water. In this context, the active compounds can be, for example, active compounds from the fields of medicine or agriculture, or else other substances having particular technical function, such as, for example, colorants. In particular, the invention relates to microemulsions of crop protection agents with a combination of water-soluble active compounds and active compounds which are virtually insoluble in water, specifically microemulsions of glufosinate and oxyfluorfen or glyphosate and oxyfluorfen.

Frequently, combinations of active compounds are employed to use the properties of the individual active compounds jointly in the application, or else because the individual active compounds in the combination are synergistic, i.e. show super-additive increases in activity. Moreover, the active compounds are usually not employed as pure substances but, depending on the area of application and the desired physical properties of the application form, in combination with certain auxiliaries, i.e. they are "formulated". In the case of a combination of active compounds of chemically different types, the person skilled in the art of formulation frequently encounters the problem of incompatibility of the individual active compounds with one another and with the auxiliaries in the joint formulation. To be able to make full use of the advantages of the combined active compounds, stable coformulations are of particular interest.

In principle, combinations of different active compounds can be formulated in various ways, depending on the prevalent biological and/or chemical-physical parameters. In general, suitable formulation possibilities in this context are, for example: wettable powders (WP), oil-in-water or water-in-oil emulsions (EW and EO, respectively), suspensions (SC), suspo-emulsions (SE) or else granules for soil application or application by scattering, or water-dispersible granules (WG). The abovementioned types of formulation are known in principle and described, for example, in: Winnacker-Küchler, "Chemische Technologie", [Chemical Technology], Volume 7, C. Hauser-Verlag, Munich, 4th edition 1986; van Valkenburg, "Pesticides Formulations", Marcel-Dekker N.Y., 1973; K. Martens, "Spray Drying Handbook", 3rd Ed., 1979, G. Goodwin Ltd. London.

If the active compounds to be combined are compounds having contrasting chemical-physical properties, the formulation possibilities are naturally limited. Thus, for example, the broad-spectrum herbicides glufosinate and glyphosate, having phosphinoyl or phosphono groups, and their salts belong to the polar hydrophilic active compounds which dissolve relatively well in water. In contrast, herbicides from the group of the diphenyl ethers such as oxyfluorfen are virtually insoluble in water.

The combined use of herbicides of the abovementioned kind is already known. In DE-A-19501986 (WO 96122692, ZA-A-96/0502), for example, synergistic combinations of glufosinate-ammonium and salts thereof with oxyfluorfen are described, and wettable powders (WP), water-dispersible granules (WDG) and oil-in-water emulsions (EW) are mentioned as possible coformulations. Other coformulations of glufosinate-ammonium and oxyfluorfen are known from U.S. Pat. No. 5,324,708 and Research Disclosure 275 (1987), 154. In addition, the preparation of granules for such active compound combinations has been described; see EP-A-448538, EP-A-0394211.

Furthermore, for example aqueous dispersions with glufosinate or salts thereof and a water-insoluble herbicide are known (JP-A-07089817). In particular, aqueous dispersions with glufosinate-ammonium and linuron, monolinuron, metolachlor or alachlor (EP-A-0244754) or with glufosinate-ammonium and diuron or simazine (EP-A-0499798) are known.

Combinations of glyphosate(salts) and oxyfluorfen are known from WO 84/03607 and EP-A-0143547.

However, none of the abovementioned formulations is a microemulsion or comprises a microemulsion. In contrast to the milky-turbid macroemulsions and suspensions, microemulsions or micellar solutions are—owing to the small particle size ($\leq 100$ nm)—optically transparent. A particular advantage of the microemulsions consists in their thermodynamic stability, owing to which microemulsions have theoretically unlimited storage-stability and shelf-life. In contrast, macroemulsions or suspensions are usually only kinetically stable, and phase separation and thus "decomposition" of the formulation may occur after a period of time which differs, depending on the individual case.

Compared to the likewise optically transparent emulsion concentrates (EC), microemulsions have additionally generally a reduced percentage by weight of solvents. Furthermore, owing to the large reduction of the interfacial tension between the aqueous and the oil phase by the emulsifier systems in question, the otherwise widely used thickeners for stabilizing the formulation can be dispensed with. Since there is a correlation between interfacial and surface tension (see Young's equations), such micellar solutions additionally frequently do not require antifoams.

A further advantage of microemulsions is the fact that the very small oil or water droplets which are present in the concentrate are preserved or converted into stable macroemulsion droplets on dilution with water. Dilution with water, which is customary prior to biological application, therefore results in spray liquors having small particle sizes, thus preventing clogging of spray apparatus. Moreover, microemulsions can advantageously be prepared with very low energy input and with technically simple stirrers, i.e. even during the production advantages result compared to the abovementioned thermodynamically instable formulations, not only in terms of materials saved, but also in terms of reduced energy costs.

Examples of preparing pesticidal microemulsions are given, inter alia, in the publications WO-A-9006681, WO-A-9314630, EP-A-0160182, EP-A-0533057, EP-A-499587, EP-A-500401, EP-A-432062, DE-A-3624910, DE-A-3235612, EP-A-648414 and EP-A-617894.

However, the microemulsions in question contain neither glufosinate-ammonium nor glyphosate(salts), and the emulsifiers, wetting agents and dispersants disclosed in the abovementioned publications are in most cases unsuitable for preparing glufosinate—and/or glyphosate-containing microemulsions; their use results in instable formulations, characterized by strong turbidity and subsequent phase separation.

Furthermore, it is known that microemulsions with glyphosate(salts) and oxyfluorfen can be prepared using mixtures of fatty amine ethoxylates of various degrees of ethoxylation (GB-A-2267825) or of fatty amine ethoxylates and quaternized cationic surfactants (U.S. Pat. No. 5565409)

in the presence of other surfactants or of compatibility agents. The emulsifiers mentioned in the publications are of an exclusively basic or cationic nature.

In addition to the abovementioned general advantages of microemulsions, it is also known, however, that microemulsions are "critical" systems insofar as they are usually sensitive toward variations in temperature and/or in exchange or in the addition of individual components. In most cases, a modification by addition of other surfactants is not possible, which makes an adaptation of the microemulsions to the active compounds and active compound combinations which are employed in each case or to other application conditions, such as the ratio of the active compounds, temperature variations during storage, climatic zones, etc., more difficult.

Hitherto, it is difficult to predict if stable microemulsions can be prepared for an individual case, and in most cases special coordination of all components and ratios is required. There is therefore in principle a demand for surfactant systems which make preparation of stable microemulsions possible.

Additionally, it is known that the effect of pesticides can be considerably increased by addition of certain surface-active substances. Thus, for example alkoxylated fatty amines have been proposed for increasing the effect of glyphosate(salts) (EP-A-0290416). Moreover, isopropylammonium salts of the esters of ortho-phosphoric acid and triethoxylated butanol as surfactant component(s) have been described to increase the biological activity of glyphosate (salts) (DE-A-4116516). Similarly, in the case of glufosinate-ammonium a strong increase in activity is observed in the presence of $C_{12}/C_{14}$-fatty alcohol diglycol ether sulfate sodium (EP-A-0476555, EP-A-0048436, EP-A-0336151 or U.S. Pat. No. 4400196). In general, alkyl polyglycol ether sulfates are additionally also known as penetration-promoting auxiliaries and activity-enhancers for a number of other herbicides, including, inter alia, herbicides of the type of the diphenyl ethers (EP-A-0476555). Consequently, there is a particular interest for formulations containing such activity-enhancers either directly as auxiliaries, or which permit their "incorporation", in disfavor of the emulsifier mixture which is technically required. The person skilled in the art requires suitable surfactant systems, so that the application properties of the formulations can be met both with respect to their stability and also with respect to the desired activity. There is therefore still an increased demand for surfactant systems which permit the effect of the formulated active compounds to develop in an advantageous manner.

The invention provides surfactant systems for liquid aqueous or aqueous-organic formulations (preparations), which comprise a mixture of one or more basic cosurfactants (surfactant component 1) and one or more anionic surfactants from the group of the acidic phosphoric esters (surfactant component 2).

The invention also provides the liquid aqueous or aqueous-organic formulations which comprise the surfactant systems according to the invention, in particular formulations which comprise (a) one or more water-soluble active compounds (active compounds of type (a)) and (b) optionally one or more water-insoluble active compounds (active compounds of type (b)), (c) optionally organic solvents, (d) the surfactant system according to the invention (component mixture (d)) and water.

The surfactant system or the corresponding formulations may additionally optionally contain further components, for example other surfactants or other active compounds and/or auxiliaries which are customary in crop protection, such as inert materials, tackifiers, wetting agents, dispersants, emulsifiers, penetrants, preservatives, antifreeze agents, solvents, fillers, carriers, colorants, antifoams, evaporation inhibitors and pH and viscosity regulators.

In the context of the invention, a basic cosurfactant is, aside from the basicity, a component which is better soluble in an oil phase than in water, which is surface-active and therefore reduces the interfacial tension between these phases, but which does not form any micellar structures in water, owing to its insufficient amphiphilicity. The substances which are labeled here as cosurfactants are characterized in particular by the fact that they do not form any aggregates in aqueous, solution, detectable, for example, by light-scattering measurements or other methods.

Suitable basic (cationogenic) cosurfactants (surfactant component 1) are, for example:

(a1) N-alkylamines, such as primary, secondary or tertiary N-alkylamines, for example having in each case 5 to 22 carbon atoms, preferably 5 to 14 carbon atoms, for example n- or i-pentyl- or hexylamine, n-octylamine, n-decylamine, n-dodecylamine or n-tetradecylamine, or unsubstituted or substituted cycloalkylamines having preferably 5 to 12 C-Atoms, for example cyclohexylamine.

(b1) oxalkylated products of the N-alkylamines, preferably products of fatty amines (for example $C_8$–$C_{22}$-fatty amines) with ethylene oxide and/or propylene oxide, in particular fatty amine ethoxylates having 8 to 18 carbon atoms in the fatty alkyl moiety and 1 to 6 ethyleneoxy units (EO), where the EO units are present attached to one or 2 chains of the amino group. Examples are coconut fatty amine ethoxylates such as Genamin C-020® (Clariant), which can formally be considered as reaction products of N,N'-bis-(2-hydroxyethyl)-alkylamine with alkylene oxides, preferably ethylene oxide and/or propylene oxide;

(c1) alkylaminepolypropyleneamines ("polyamines"), such as, for example, coconut alkylpropylenediamines, -triamines or -polyamines (for example ®Dinoram C, ®Trinoram C or ®Polyram C; all from Elf Atochem), (d1) oxalkylated products of amides or N-substituted amides, such as carboxylic acid ethanolamides, preferably based on alkanecarboxylic acids having 8 to 18 carbon atoms and ethanolamine or diethanolamine, for example Comperlan LS® (Henkel), or such as oxalkylated N-(aminoalkyl)-amides or N,N-bis-(aminoalkyl)-amides, (e1) alkylamidopropylamines, preferably those based on a $C_8$–$C_{18}$-alkanecarboxylic acid and diamines, such as DMAPA (=N,N-dimethylpropylamine), for example oleoylaminopropyidimethylamine (®Mackine 501, Mc Intyre).

Surfactants from the group of the acidic phosphoric esters (surfactant component 2) which can be used according to the invention are, for example, surface-active compounds having one or more phosphate groups which are not fully esterified and where the esterified acid radicals are esterified with compounds from the following group of alcohol components:

(a2) alkanols (for example isoalkanols) having, for example, 1 to 22 carbon atoms, preferably 1 to 12 carbon atoms, in particular from 4 to 12 or 4 to 8 carbon atoms, or unsubstituted or substituted cycloalkanols having preferably 5 to 12 C-atoms, e.g. cyclohexanol, alkylcyclohexanoles, cyclopentanol, (b2) oxalkylated alkanols having up to 24 carbon atoms in the alkyl radical and 1 to 150 alkyleneoxy units in the alkyleneoxy or polyalkyleneoxy moiety, preferably those having 4 to 22 carbon atoms, in particular 10 to 20 carbon atoms in the alkyl radical and 1 to 60, in particular 3 to 30 alkyleneoxy units in the alkyleneoxy or polyalkyleneoxy moiety, (c2) phenol or oxalkylated phenol, where the phenyl radical is in each case unsubstituted or substituted by one, two or three alkyl radicals having preferably in each case 4 to 12 carbon atoms or by one, two or three aryl or arylalkyl radicals having 6 to 12 carbon atoms, and having, in the oxalkylated case, 1 to 150 alkyleneoxy units in the alkyleneoxy or polyalkyleneoxy moiety, preferably oxalkylated phenol having 1 to 20 alkyleneoxy units or oxalkylated phenol which is substituted by 1 to 3 alkyl radicals having in each case 4 to 12 carbon atoms and has 1 to 60, in particular 4 to 30, alkyleneoxy units, or oxalkylated phenol which is substituted by one, two or three aryl or arylalkyl radicals having 6 to 12 carbon atoms and has 1 to 100, in particular 10 to 30, alkyleneoxy units, and (d2) oxalkylated alkylamines having, for example, up to 24 carbon atoms in the alkyl moiety and 1 to 150 alkyleneoxy units in the polyalkyleneoxy moieties, so that the tensides are e.g. phosphated alkoxylated alkylamines such as ethoxylated $C_8$–$C_{22}$-fatty amines.

For the respective abovementioned alkyleneoxy units, preference is given to ($C_1$–$C_4$) alkyleneoxy units, for example ethyleneoxy, propyleneoxy and butyleneoxy units, in particular ethyleneoxy units.

Phosphoric esters which are particularly preferably used are, for example:

phosphated ethoxylated long-chain alcohols or fatty alcohols having 10 to 18 carbon atoms in the alkyl radical and 1 to 30 ethyleneoxy units in the polyethyleneoxy moiety, for example Rhodafac RS 710® (Rhone-Poulenc), Crodafos T 10 A® (Croda) or Crafol AP 240® (Henkel) or Servoxyl VPDZ 20/100® (Hüls), phosphated ethoxylated phenol or alkylphenol having 4 to 12 carbon atoms in the alkyl radical and in each case 1 to 30 ethyleneoxy units in the polyethyleneoxy moiety, for example Rhodafac PA/19® (Rhone-Poulenc), phosphated ethoxylated tristyrylphenol having 1 to 150 ethyleneoxy units in the polyethyleneoxy moiety, for example Soprophor 3D33® (Rhone-Poulenc).

Additionally, the surfactant system may comprise other surfactants, without loosing the abovementioned advantageous properties of the surfactant system. Thus, it is optionally possible to incorporate, for example, anionogenic surfactants, such as alkyl polyglycol ether sulfates or alkyl polyglycol ether carboxylates, into the formulations. Examples of such anionogenic surfactants are Genapol LRO® (Clariant) and Marlowet 4538® (Hüls).

Using the surfactant systems according to the invention, it is now surprisingly possible to prepare optically transparent, thermodynamically stable and liquid pesticidal microemulsions of water-soluble active compounds such as glyphosate(salts) and/or glufosinate-ammonium in combination with water-insoluble active compounds of type (b), such as, for example, oxyfluorfen, diclofop-methyl, fenoxaprop-ethyl or fenoxaprop-Pethyl.

In addition, the surfactant system according to the invention has a favorable influence on the herbicidal activity of water-soluble active compounds such as glyphosate(salts) or glufosinate-ammonium in combination with the active compounds of type (b).

The surfactant system according to the invention accordingly also permits the microemulsification of oil phases or oil-soluble active compounds other than those listed here. Furthermore, it also provides access to microemulsions of active compounds other than the abovementioned water-soluble active compounds, for example of herbicides from the group of the diphenyl ethers, carbamates, thiocarbamates, haloacetanilides, phenoxyphenoxycarboxylic acid derivatives and heteroaryloxyphenoxyalkanecarboxylic acid derivatives, such as quinolyloxy, quinoxalyloxy, pyridyloxy, benzoxalyloxy and benzothiazoleyloxyphenoxyalkanecarboxylic esters, which usually have suitable solubility in the oil phase.

In some instances, however, oil-soluble, virtually water-insoluble active compounds from the group which usually comprises active compounds of varying solubility are also suitable, for example active compounds from the group of the cyclohexanedione derivatives, imidazoleinones, pyrimidyloxypyridinecarboxylic acid derivatives, pyrimidyloxybenzoic acid derivatives, sulfonylureas, triazoleopyrimidinesulfonamide derivatives, and also S-(N-aryl-N-alkylcarbamoylmethyl)dithiophosphoric esters.

Correspondingly, active compounds from the group of the safeners, growth regulators, insecticides and fungicides are also suitable as component (b), or, if they are readily soluble in water, as components (a).

The fact that the surfactant system can be easily transferred to other combinations of water-insoluble and water-soluble active compounds demonstrates the flexibility of the surfactant system. This compatibility with other oil or water phases is likewise a considerable practical advantage of the component mixtures described.

For the abovementioned reasons, the invention in particular provides surfactant systems for liquid pesticidal compositions comprising (a) one or more compounds of the formula (1) or salts thereof

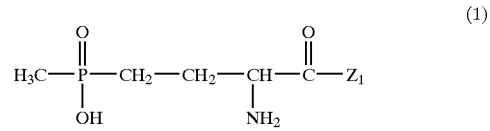

(1)

in which $Z_1$ is a radical of the formula —OM, —NHCH($CH_3$)CONHCH($CH_3$)$CO_2$M or —NHCH($CH_3$)CONHCH[$CH_2$CH($CH_3$)$_2$]$CO_2$M and M=H or a salt-forming cation, and/or one or more compounds of the formula (2) or salts thereof

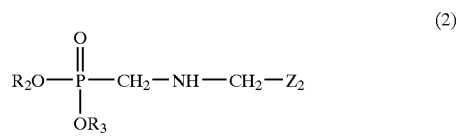

(2)

in which $Z_2$ is a radical of the formula CN or $CO_2R_1$, in which $R_1$=Q or a salt-forming cation and Q=H, alkyl, alkenyl, alkoxyalkyl or $C_6$–$C_{10}$-aryl, which is unsubstituted or substituted and is preferably unsubstituted or substituted by one or more radicals, selected from the group consisting of alkyl, alkoxy, halogen, $CF_3$, $NO_2$ and CN, and $R_2,R_3$ in each case independently of one another are H, alkyl, $C_6$–$C_{10}$-aryl, which is unsubstituted or substituted and is preferably unsubstituted or substituted by one or more radicals selected from the group consisting of alkyl, alkoxy, halogen, $CF_3$, $NO_2$ and CN, or are biphenyl or a salt-forming cation, and/or one or more compounds of the formula (3)

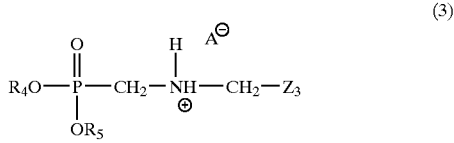

(3)

in which

Z$_3$ is a radical CN or $CO_2Q'$ in which Q'=H, alkyl, alkenyl, alkoxyalkyl or $C_6$–$C_{10}$-aryl which is unsubstituted or substituted and is preferably unsubstituted or substituted by one or more radicals selected from the group consisting of alkyl, alkoxy, halogen, $CF_3$, $NO_2$ and CN, and $R_4$ and $R_5$ are each H, alkyl or $C_6$–$C_{10}$-aryl which is unsubstituted or substituted and is preferably unsubstituted or substituted by one or more radicals selected from the group consisting of alkyl, alkoxy, halogen, $CF_3$, $NO_2$ and CN, and A is a salt-forming anion, and (b) optionally one or more water-insoluble active compounds, in particular from the group of the herbicides mentioned as being preferred, (c) optionally one or more organic solvents, (d) the abovementioned surfactant system of one or more basic cosurfactants and one or more surfactants from the group of the acidic phosphoric esters.

In the formulae (1) to (3) and in the formulae used hereinbelow, the radicals alkyl, alkoxy and the corresponding substituted radicals may in each case be straight-chain or branched in the carbon skeleton. Unless specifically defined otherwise, for these radicals preference is given to the lower carbon skeletons, for example having 1 to 4 carbon atoms or, in the case of unsaturated groups, having 2 to 4 carbon atoms. Alkyl radicals, also in the composed meanings, such as alkoxy (alkanols) etc., are, for example, methyl, ethyl, n- or i-propyl, n-, i-, t- or 2-butyl, pentyl, hexyl, such as n-hexyl, i-hexyl and 1,3-dimethylbutyl, heptyl, such as n-heptyl, 1-methylhexyl, 2-ethylhex-1-yl and 1,4-dimethylpentyl.

Halogen is, for example, fluorine, chlorine, bromine or iodine, haloalkyl, -alkenyl and -alkynyl are alkyl, alkenyl and alkynyl, respectively, which are partially or fully substituted by halogen, preferably by fluorine, chlorine, and/or bromine, in particular by fluorine or chlorine, for example $CF_3$, $CHF_2$, $CH_2F$, $CF_3CF_2$, $CH_2FCHCl_2$, $CCl_3$, $CHCl_2$, $CH_2CH_2Cl$; haloalkyl is, for example, $OCF_3$, $OCHF_2$, $OCH_2F$, $CF_3CF_2O$, $OCH_2CF_3$ and $OCH_2CH_2Cl$; this applies correspondingly to haloalkenyl and to other halogen-substituted radicals.

Aryl is a monocyclic, carbocyclic aromatic ring which, in the substituted case, also includes a bi- or polycyclic aromatic system which contains at least one aromatic ring and optionally other aromatic rings or partially unsaturated or saturated rings; aryl is, for example, phenyl, naphthyl, tetrahydronaphthyl, indenyl, indanyl, pentalenyl, fluorenyl and the like, preferably phenyl; Aryl is a mono-, bi- or polycyclic aromatic system, for example phenyl, naphthyl, tetrahydronaphthyl, indenyl, indanyl, pentalenyl, fluorenyl and the like, preferably phenyl; aryloxy is preferably an oxy radical which corresponds to the abovementioned aryl radical, in particular phenoxy.

Substituted radicals, such as, for example, substituted alkyl, aryl or phenyl are, for example, a substituted radical which is derived from the unsubstituted skeleton, where the substituents are, for example, one or more, preferably 1, 2 or 3, radicals selected from the group consisting of halogen, alkoxy, haloalkoxy, alkylthio, hydroxy, amino, nitro, cyano, azido, alkoxycarbonyl, alkylcarbonyl, formyl, carbamoyl, mono- and dialkylaminocarbonyl, substituted amino, such as acylamino, mono- or dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals corresponding to the abovementioned saturated hydrocarbon-containing radicals, such as alkenyl, alkynyl, alkenyloxy, alkynyloxy, etc. In the case of radicals having carbon atoms, preference is given to those having 1 to 4 carbon atoms, in particular 1 or 2 carbon atoms. Preference is generally given to substituents from the group consisting of halogen, for example fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano. Particular preference here is given to the substituents methyl, methoxy and chlorine.

Preferred compounds of the formulae (1), (2) and (3) are those in which $Z_1$ is a radical of the formula —OM and M=H or a salt-forming cation, $Z_2$ is a radical of the formula CN or $CO_2R_1$ in which $R_1$=Q or a salt-forming cation and where Q=H, $(C_1$–$C_{12})$alkyl, $(C_2$–$C_{12})$alkenyl, $(C_1$–$C_6)$alkoxy-$(C_1$–$C_6)$alkyl or $(C_6$–$C_{10})$aryl which is unsubstituted or substituted and is preferably unsubstituted or substituted by one or more radicals from the group consisting of $(C_1$–$C_4)$alkyl, $(C_1$–$C_4)$alkoxy, halogen, $CF_3$, $NO_2$ and CN, $R_2,R_3$ in each case independently of one another are H, $(C_1$–$C_4)$alkyl, $(C_1$–$C_{10})$aryl which is unsubstituted or substituted and is preferably unsubstituted or substituted by one or more radicals from the group consisting of $(C_1$–$C_4)$alkyl, $(C_1$–$C_4)$alkoxy, halogen, $CF_3$, $NO_2$ and CN, or are biphenyl or a salt-forming cation, $Z_3$ is a radical CN or $CO_2Q'$ in which Q'=H, $(C_1$–$C_{12})$alkyl, $(C_2$–$C_{12})$alkenyl, $(C_1$–$C_6)$alkoxy-$(C_{1–C6})$alkyl or $(C_6$–$C_{10})$aryl which is unsubstituted or substituted and is preferably unsubstituted or substituted by one or more radicals from the group consisting of $(C_1$–$C_4)$alkyl, $(C_1$–$C_4)$alkoxy, halogen, $CF_3$, $NO_2$ and CN, $R_4$ and $R_5$ are each H, $(C_1$–$C_4)$alkyl or $(C_6$–$C_{10})$aryl which is unsubstituted or substituted and is preferably unsubstituted or substituted by one or more radicals from the group consisting of $(C_1$–$C_4)$alkyl, $(C_1$–$C_4)$alkoxy, halogen, $CF_3$, $NO_2$ and CN, and/or, A is a salt-forming anion, such as, for example, a halide, sulfate, nitrate, phosphate, carbonate, bicarbonate anion or an acid anion of a carboxylic acid or another organic acid.

The compounds of the formula (1) contain an asymmetric carbon atom. The L-enantiomer is considered to be the biologically active isomer. Thus, the formula (1) embraces all stereoisomers and mixtures thereof, in particular the racemate and the respective biologically active enantiomer. Examples of active compounds of the formula (1) are the following:

Glufosinate and its ammonium salt in racemic form,
The L-enantiomer of glufosinate and its ammonium salt,
Bilanafos/bialaphos, i.e. L-2-amino-4-[hydroxy(methyl) phosphinoyl]-butanoyl-L-alaninyl-L-alanine and its sodium salt.

The racemate of glufosinate-ammonium on its own is usually applied in dosages between 200 and 1000 g of a.i./ha (=gram of active substance per hectare). At these dosages, glufosinate-ammonium is effective in particular when it is taken up via the green parts of the plants; see "The Pesticide Manual" 10th Edition, British Crop Protection Council 1994, p. 541. Glufosinate-ammonium is mainly employed for controlling broad-leaved weeds and weed grasses in plantation crops and on uncultivated land and, by means of special application techniques, also for inter-row treatment in agricultural row crops such as maize, cotton and the like. Use in transgenic crops which are resistant to or tolerant of the active compound in question are becoming increasingly important.

Since the active compound glufosinate-ammonium is degraded microbially in the soil within a few days, no long-term action can be observed. Similarly, this is also true for the related active compound bilanafos/bialaphos; see "The Pesticide Manual" 10th Edition, British Crop Protection Council 1994, p. 98.

The compounds of the formulae (2) and (3) are N-(phosphonoalkyl)glycine, and thus derivatives of the amino acid glycine. The herbicidal properties of N-(phosphonomethyl)glycine ("glyphosate") are described, for example, in U.S. Pat. No. 3,799,758. In crop protection formulations, glyphosate is usually employed in the form of the water-soluble salts, the isopropylammonium salt ("IPA-glyphosate") being of particular importance in the context of the present invention.

In general, the surfactant system according to the invention (component mixture (d)) is suitable for microemulsifying oil phases in water or, if the individual components are selected appropriately, of aqueous phases in oil. Depending on the composition, this gives access to microemulsions which can be diluted either with water or with oil, while maintaining the micellar structure. Furthermore, in the absence of the oil phases comprising the oil soluble active compounds of type (b), thin aqueous solutions of the active compounds described under (a) are obtained.

The invention therefore preferably provides the oil-in-water microemulsions with the components (a) to (d), in particular those with one or more diphenyl ethers dissolved in an organic solvent, a herbicide from the group of the azole herbicides, phenoxyphenoxycarboxylic acid derivatives and heteroaryloxyphenoxycarboxylic acid derivatives.

Here, the term "diphenyl ether" embraces chemical compounds from the group of the diphenyl ether herbicides, their equivalents, metabolites, salts, esters and derivatives. Diphenyl ether herbicides are composed of two substituted benzene rings which are linked via an oxygen atom. They are usually employed for controlling broad-leaved weeds and weed grasses by the pre- or post-emergence method. Depending on the substitution and the light input, which is relevant for the herbicidal action, a distinction is made between diphenyl ethers which are substituted in position 2,4 or 2,4,6 and diphenyl ethers which are substituted in position 3 or 3,5.

The group of the diphenyl ether herbicides includes in particular acifluorfen and the corresponding alkali metal salts, aclonifen, bifenox, chlomethoxyfen, fluoroglycofen, fomesafen, lactofen, nitrofen, oxyfluorfen and mixtures of these compounds. The abovementioned compounds are described, for example, in "The Pesticide Manual" 10th Edition, British Crop Protection Council 1994 and in the literature cited therein, and they are known as herbicides of the type of the protoporphyrinogen oxidase inhibitors.

The term "azole-herbicides" includes chemical compounds which comprise one or more substituted heterocycles having one or more nitrogen atoms. Depending on the number of nitrogen atoms in the parent heterocycle, these compounds are then referred to as mono-, di- or else triazole herbicides. The group of the "azole herbicides" includes, in particular, oxadiazone.

Likewise, this compound is described in "The Pesticide Manual" 10th Edition, British Crop Protection Council 1994 and in the literature cited therein, and it is known as a herbicide of the type of the protoporphyrinogen oxidase inhibitors.

Suitable oil-soluble herbicides from the group of herbicides of the type of the phenoxyphenoxy- and heteroaryloxyphenoxycarboxylic acid derivatives are, for example, a) phenoxyphenoxycarboxylic acid derivatives, for example,
methyl 2-(4-(2,4-dichlorophenoxy)phenoxy) propionate (diclofop-methyl)
butyl 2-(4-(4-cyano-2-fluorophenoxy)phenoxy) propionate and its 2-(R)-enantiomer (cyhalofop-butyl)
methyl 2-(4-(2-chloro-4-trifluoromethylphenoxy) phenoxy)propionate (see DE-A-2433067)
methyl 2-(4-fluoro-4-trifluoromethylphenoxy) phenoxy)propionate (see U.S Pat. No. 4808750)
methyl 2-(4-(4-trifluoromethylphenoxy)phenoxy) propionate (see DE-A-2433067), b) "mononuclear" heteroaryloxyphenoxyalkanecarboxylic acid derivatives, for example
ethyl 2(4-(3,5-dichloropyridyl-2-oxy)phenoxy) propionate (see EP-A-2925)
methyl 2-(4-(3-chloro-5-trifluoromethyl-2-pyridyloxy) phenoxy)-propionate (see EP-A-3890),
methyl 2-(4-(3-chloro-5-trifluoromethyl-2-pyridyloxy) phenoxy)-propionate and its (R) enantiomer (haloxyfop-methyl or haloxyfop-P-methyl, see EP-A-3890) and the corresponding ethoxyethyl ester (haloxyfop-etotyl or haloxyfop-P-etotyl),
propargyl 2-(4-(5-chloro-3-fluoro-2-pyridyloxy) phenoxy)propionate and its (R)-enantiomer (EP-A-191736, clodinafop-propargyl),
butyl 2-(4-(5-trifluoromethyl-2-pyridyloxy)phenoxy) propionate and its (R)-enantiomer (fluazifop-butyl or fluazifop-P-butyl), C) "dinuclear" heteroaryloxyphenoxyalkanecarboxylic acid derivatives, for example,
methyl and ethyl (R)-2-(4-(6-chloro-2-quinoxalyloxy) phenoxy)-propionate (quizalofop-P-methyl and -ethyl, respectively) or the corresponding 2-isopropylideneaminooxyethyl ester (propaquizafop),
ethyl 2-(4-(6-chlorobenzoxazole-2-yl-oxy)phenoxy) propionate (fenoxaprop-ethyl), its (R)-enantiomer (fenoxaprop-P-ethyl),
tetrahydrofur-2-ylmethyl 2-(4-(6-chloroquinoxalyloxy)phenoxy)-propionate and its (R)-enantiomer (see EP-A-323 727).

The compounds mentioned with the common name are also described in "The Pesticide Manual" 11th edition, British Crop Protection Council 1997, and in most cases they are known as inhibitors of the fatty acid biosynthesis in plants.

The ratios by weight (a):(b) of the combined active compounds of type (a) and (b) can vary within wide limits and depend especially on the activity or the usual application rate of the active compounds employed. The ratios by weight are generally between 1000:1 and 1:1, preferably from 100:1 to 1:1, in particular from 50:1 to 1:1, and in the case of the herbicides of the formula (1), (2) or (3) and diphenyl ether herbicides preferably between 10:1 and 1:1. For combinations of diphenyl ether herbicides with herbicides of type (a), in particular glufosinate-ammonium, the following ratios by weight (a):(b) are preferred:

with acifluorfen, 10:1 to 2:1, in particular 8:1 to 3:1.
with bifenox, 10:1 to 2:1, in particular 8:1 to 3:1.
with fluoroglycofen, 100:1 to 10:1, in particular 50:1 to 10:1.
with fomesafen, 10:1 to 2:1, in particular 8:1 to 3:1.
with lactofen, 10:1 to 2:1, in particular 8:1 to 3:1.
with oxyfluorfen, 10:1 to 2:1, in particular 8:1 to 3:1.

In general, application rates of from 100 to 600 g of a.i./ha of herbicide of type (a), preferably glufosinate-ammonium, and from 50 to 150 g of a.i./ha of the active compounds of type (b), in particular oxyfluorfen or lactofen, may be employed.

The optimum choice of the ratios by weight and the application rates depends, in particular, on the development stage of the broad-leaved weeds or weed grasses in question, of the prevailing weed ranges, on environmental factors and climatic conditions, so that the abovementioned ratios by weight and application rates have to be checked in the individual case. For combined use, the application rate of the herbicides in question is considerably below the application rates for the individual application for the same herbicidal effect, so that thermodynamically stable formulations which comprise both active compound components result in a particularly high biological activity, and a reduced content of active compound.

In the context of the present invention, the term "organic solvents" (component (c)) denotes, for example, unpolar solvents, polar protic or aprotic polar solvents and mixtures thereof. Examples of solvents in the context of the invention are aliphatic or aromatic hydrocarbons, such as, for example, mineral oils, or toluene, xylenes or naphthalene derivatives;

halogenated aliphatic or aromatic hydrocarbons, such as methylene chloride or chlorobenzene;

ethers, such as diethyl ether, tetrahydrofuran (THF), dioxane, alkylene glycol monoalkyl ethers and dialkyl ethers, such as, for example, propylene glycol monomethyl ether, propylene glycol monoethyl ether, ethylene glycol monomethyl ether or monoethyl ether, diglyme and tetraglyme;

amides, such as dimethylformamide (DMF), dimethylacetamide, dimethylcaprylamide, dimethylcaprinamide (®Hallcowide) and N-alkylpyrrolidones;

ketones, such as acetone;

esters based on glycerol and carboxylic acids, such as glycerol mono-, di- and triacetate, phthalic esters;

lactams;

carbonic diesters;

nitriles, such as acetonitrile, propionitrile, butyronitrile and benzonitrile;

sulfoxides and sulfones, such as dimethyl sulfoxide (DMSO) and sulfolane;

oils, for example based on vegetables, such as corn oil and rapeseed oil.

In many cases, combinations of different solvents which additionally contain alcohols, such as methanol, ethanol, n- and i-propanol, n-, i-, t- and 2-butanol, are also suitable.

In the case of the monobasic aqueous-organic solutions, completely or substantially water-miscible solvents or solvent mixtures are suitable.

Suitable for preparing the microemulsions are essentially those solvents which predominantly become a component of the organic phase, i.e. solvents or solvent mixtures which are not or only sparingly miscible with water. In addition, it is also possible to mix, if appropriate, solvents which are partially or indefinitely soluble in water.

In the context of the present invention, preferred organic solvents are aromatic solvents, such as toluene, o-, m- or p-xylene and mixtures thereof, 1-methylnaphthalene, 2-methylnaphthalene, 6–16 C aromatic mixtures, such as, for example, the Solvesso®-series (ESSO) including the types Solvesso® 100 (B.p. 162–177° C.), Solvesso® 150 (B.p. 187–207° C.) and Solvesso 200 (B.p. 219–282° C. (1–12C)alkyl phthalates, specifically (4–8C)alkyl phthalates, water-immiscible ketones, such as, for example, cyclohexanone or isophorone, or 6–20C-aliphatics, which may be linear or cyclic, such as the products of the Shellsol®-series, types T and K, or BP-n paraffins, esters, such as glycerol triacetate, and the polar organic solvents N-methylpyrrolidone and Dowanol® PM (propylene glycol monomethyl ether).

The components which may additionally be present as formulation auxiliaries in the formulations according to the invention are, for example, water-insoluble solid inert materials, which often make an advantageous contribution to the stability of the formulation. This may prevent or delay, for example, formation of macrophases, sedimentation of solid phases, and the like. In this context, suitable inert materials are resins or resin-like substances of natural or synthetic origin which are soluble in the oil phase, for example natural resins such as colophony (rosin, rosin gum) and tannin. The resins may be added, for example, in amounts of up to 30% by weight, preferably up to 20% by weight, in particular up to 5% by weight, based on the weight of a formulation.

The auxiliaries which are required for preparing the abovementioned formulations, such as, in particular, surfactants and cosurfactants, are known in principle and are described, for example, in: McCutcheon's "Detergents and Emulsifiers Annual", MC Publ. Corp., Ridgewood N.J.; Sisley and Wood, "Encyclopedia of Surface active Agents", Chem. Publ. Co. Inc., N.Y. 1964; Schönfeld, "Grenzfl ächenaktive Äthylenoxidaddukte" [Surface-active ethylene oxide adducts], Wiss. Verlagsgesellschaft, Stuttgart 1976; Winnacker-Küchler, "Chemische Technologie", Volume 7, C. Hauser-Verlag, Munich, 4th edition 1986, and the literature cited in these publications.

Whereas the chemical "structure" of the individual utilizable components is sufficiently described therein, the properties of mixtures of such components for the formulation of a certain active compound system can not be predicted from the abovementioned handbooks. This is true even if component mixtures are used with which microemulsions have already been obtained for other active compounds—as is illustrate d by Table 1 (see further below). If, in the present case, for example a surfactant combination is used with which microemulsions have already been obtained and described for other active compounds (cf. DE-A-36234910), it is precisely the case for combinations of glufosinate-ammonium and oxyfluorfen that no microemulsions but instable multi-phase systems are found (see Examples 1 and 4).

Similarly, using, instead of the ethoxylated fatty amine employed as "coemulsifier" in Examples 1 and 4, compounds which have already been described as cosurfactants in another context—such as, for example, n-butanol (Example 2)—likewise gives a multi-phase system instead of a microemulsion. Furthermore, it is not correct to assume that n-butanol is just too hydrophobic to be suitable for use as a cosurfactant for the formation of a microemulsion in the present case. As is shown by Example 3 in Table 1, a microemulsion is not obtained, even if the HLB value is increased. Furthermore, in the case of glufosinate-ammonium and oxyfluorfen for neutralized phosphoric esters in the presence of basic cosurfactant (Examples 5–7), phase separation is observed.

Starting from these component mixtures, which do not give a stable microemulsion of the active compound combination (a) and (b), it was consequently not to be expected that microemulsions for the active compounds described under (a) and (b) could be prepared by using the surfactant system of the invention. This is true in particular for mixtures of basic cosurfactants (cationogenic component) and acidic phosphoric esters (anionogenic component): specifically for such "catanionogenic" surfactant mixtures, water-insoluble crystalline precipitates are expected. A priori, they therefore seem to be entirely unsuitable for use as emulsifiers. However, surprisingly, they are precisely particularly suitable for microemulsifying the active compounds described under (a) and (b). This is illustrated by the examples listed in Table 2 (see further below) which give an idea of the chemical flexibility of the component mixtures disclosed. Thus, acidic phosphoric esters of various chemical origin can be employed, such as phosphated ethoxylated fatty alcohols based on various fatty alcohols (Example I and Example III), ethoxylated nonylphenol phosphates (Example IV) or else ethoxylated tristyrylphenol phosphates (Example V). Apparently, even the degree of ethoxylation of the phosphoric esters plays only a minor role, as can be seen from Example II. Furthermore, it is likewise possible to use chemically different components as basic cosurfactants, such as alkylamines based on various alkyls (Example I and Example VI), or aminoethoxylates (Example VII). Finally, Example VII illustrates that even basic carboxamides can be employed as cosurfactant, or acidic ethoxylated aryl phosphates as surfactant.

The chemical diversity that is possible permits the optimum adaptation of the surfactant system employed to the technical requirements that have to be met in the individual case. However, it has to be taken into account that mixtures according to component (d) are particularly effective precisely when they contain excess basic cosurfactant (Examples I–VII, IX–XIV) or excess acidic phosphoric ester (Example VIII). Preferred molar ratios (based on equivalents of the acidic or basic groups) of the components of acidic phosphoric esters: basic cosurfactant are in particular 1:1.01–1:100 or 1:0.01–1:0.99, preferably a ratio of from 1:2 to 1:4, for example approximately 1:2, 1:3 or 1:4, or of from 1:0.5 to 1:0.25, for example 2:1, 3:1 or 4:1. Consequently, mixtures which comprise the two surfactant components (1) and (2) in non-equimolar amounts are particularly suitable for microemulsification. The pH of the formulation is preferably established so that the phase separation described above does not occur—in the case of glufosinate-ammonium preferably in the range close to pH=7. If the pH is not from the beginning in the neutral range, as in the case of Examples VII and VIII, it can be adjusted, for example by using acetic acid (Examples I–VI, IX, X and XII–XIV).

Anionogenic surfactants, such as alkyl polyglycol ether sulfates or alkyl polyglycol ether carboxylates on their own, i.e. without the surfactant system according to the invention, do not give microemulsions for mixtures of (a) and (b), since their presence has a "destabilizing" effect. The use of such anionogenic surfactants alone for mixtures of (a) and (b) usually results in thermodynamically unstable systems, such as the macroemulsions described in DE-A-19501986. However, surprisingly, even alkyl polyglycol ether sulfates or alkyl polyglycol ether carboxylates give, in combination with sufficient hydrophobic primary N-alkylamines as basic component and acidic phosphoric esters as anionogenic component in accordance with component mixture (d), thermodynamically stable finished formulations (Examples IX and X).

As can furthermore be seen from Example XI, the component mixtures described under (d) can also be employed for microemulsifying active compounds which are insoluble in water, such as oxyfluorfen, in the presence of glyphosate.

N-alkylpyrrolidones as components of pesticidal microemulsions are described in the patents U.S Pat. No. 5338762, U.S Pat. No. 5326789, U.S Pat. No. 5317042, U.S Pat. No. 5298529, U.S Pat. No. 5300529 and WO-A-9213454. The surfactant system (d) according to the invention permits the microemulsification of combinations of the active compounds (a) and (b) even independently of the presence of the component N-methylpyrrolidone (NMP). This is immediately evident from Example XII.

Microemulsions or micellar solutions, which are prepared in accordance with the present invention, comprise water. Part of the water originates from the residual water which is present in commercially available surfactants or surfactant mixtures, and another part originates from the aqueous solution of the herbicides of type (a); in order to actually obtain a microemulsion with the surfactant mixtures described, additional water is generally required.

Even in the absence of an organic phase or in the presence of polar solvents which are miscible indefinitely with water, such as, for example, N-methylpyrrolidone (NMP), the surfactant system (d) according to the invention gives in combination with active compounds of type (a) single-phase stable aqueous solutions. This is illustrated by the examples in Table 3.

With the aid of the component mixtures (d), it is therefore possible to prepare preferably liquid preparations of glufosinate or glyphosate or salts thereof or of other substances which are readily soluble in water, which comprise (a) 1 to 50% by weight, preferably 5 to 20%, of the active compound of the abovementioned type (a), (b) 0 to 70% by weight, preferably 0 to 10%, of the active compound of the abovementioned type (b), (c) 0 to 60% by weight, preferably 0 to 30%, of organic solvents, (d) 3 to 70% by weight, preferably 10 to 40%, of the component mixture (d) according to the invention (surfactant system), (e) 0 to 20% by weight, preferably 0 to 15%, of other anionogenic surfactants, such as alkyl polyglycol ether sulfates or alkyl polyglycol ether carboxylates, (f) 0 to 20% by weight, preferably 0 to 15% by weight, of customary formulation auxiliaries, (g) 0.1 to 60% by weight, preferably 10 to 40%, of water, where the ratio by weight of the herbicides (a) to the surfactants mentioned under (e)—based on the detergent surfactant in question—is preferably 1:1 to 1:10, in particular 1:1 to 1:5.

Particular preference is given here to microemulsions having a content of (a) 5 to 20% by weight of active compound of the abovementioned type (a), (b) 1 to 10% by weight of the active compound of the abovementioned type (b), (c1) 5 to 30% by weight of organic solvents which form one phase with the active compound (b), (c2) 0 to 30% by weight of water-soluble organic solvents, where the total proportion of solvents (c1)+(c2) is preferably 5 to 30% by weight, (d) 10 to 40% by weight of the component mixture (d) according to the invention (surfactant system), (e) 0 to 20% by weight, preferably 0 to 15%, of other anionogenic surfactants, such as alkyl polyglycol ether sulfates or alkyl polyglycol ether carboxylates, (f) 0 to 20% by weight, preferably 0 to 10% by weight, of customary formulation auxiliaries, (g) 10 to 40% by weight of water.

Preference is furthermore also given to aqueous single-phase solutions of the herbicides (a) having a content of the surfactant system (d) according to the invention. These solutions represent a favorable form of application of the herbicides (a). Preference is here given to herbicidal aqueous single-phase solutions having a content of (a) 1 to 50% by weight, preferably from 5 to 20% by weight, of the active compound of the abovementioned type (a), (d) 3 to 70%, preferably 5 to 50%, of the component mixture (d) according to the invention (surfactant system), (c) 0 to 40% by weight of organic solvents which can be admixed without phase separation, (e) 0 to 20% by weight, preferably 0 to 15%, of other anionogenic surfactants, such as alkyl polyglycol ether sulfate or alkyl polyglycol ether carboxylates, (f) 0 to 20% by weight, preferably 0 to 15% by weight, of customary formulation auxiliaries, (g) 10 to 40% of water.

The solvents which can be admixed for preparing the aqueous single-phase solution are in particular indefinitely or substantially water-miscible organic solvents, such as, for example, N-methylpyrrolidone (NMP), dimethylformamide (DMF), dimethylacetamide (DMA) or propylene glycol monomethyl ether.

Customary formulation auxiliaries (f) are, for example, the abovementioned inert materials, antifreeze agents, evaporation inhibitors, preservatives, colorants, antifoams, and the like; preferred formulation auxiliaries (f) are the water-insoluble inert materials, (for example oil-soluble resins) up to 30% by weight, antifreeze agents and evaporation inhibitors, such as glycerol or ethylene glycol, for example in an amount of from 2 to 10% by weight, and preservatives, for example Mergal K9N® (Riedel) or Cobate C®, antifoams, such as ®Fluowet PL 80 (Clariant) in amounts of from 0.001 to 1% by weight in the customary use concentrations for the agents which are specifically employed in each case.

The liquid formulations according to the invention can be prepared by processes which are customary in principle, i.e. by mixing the components with stirring, shaking or by means of static mixing processes. The resulting liquid formulations are stable and have good storage stability.

Additionally, the liquid formulations in many instances have favorable application properties. As can be seen, for example, from Table 4 (see further below), the measurable herbicidal effect of the active compounds glufosinate-ammonium and oxyfluorfen formulated according to the invention in the form of a microemulsion in accordance with formulation I is clearly higher than that of the same active compounds, which are however formulated in the form of a macroemulsion. In general, this applies correspondingly also to other formulations according to the invention. Consequently, the formulations according to the invention are particularly suitable for controlling undesirable plant growth.

Unless defined otherwise, the amounts given in the examples below are based on the weight. The examples of Table 1 relate to comparative examples (=examples which are not according to the invention) which do not give microemulsions. Examples of microemulsions according to the invention are listed in Table 2. Table 3 additionally lists examples of single-phase systems according to the invention. Table 4 contains comparative biological results of the herbicidal activity of the formulations described.

TABLE 1

Examples of formulations which do not give microemulsions (Comparative Examples)

|  | 1 | 2 | 3 | 4 | 5 | 6 | 7 |
|---|---|---|---|---|---|---|---|
| Glufosinate-ammonium | 12.01 | 10.00 | 10.00 | 10.00 | 12.01 | 10.00 | 10.00 |
| Oxyfluorfen | 2.40 | 2.00 | 2.00 | 2.00 | 2.40 | 2.00 | 2.00 |
| [i-$C_{13}$—O-(EO)$_{10}$]$_n$ – PO$_{4-n}$H$_{3-n}$[1] |  |  | 20.00 | 20.00 | 20.00 |  |  |
| [$C_{12}/C_{18}$—O-(EO)$_{10}$]$_n$ – PO$_{4-n}$H$_{3-n}$[2] |  |  |  |  |  | 20.00 | 20.00 |
| [(Tri-Sty-)Phe-O-(EO)$_{16}$]$_n$ – PO$_{4-n}$H$_{3-n}$ + TEA[3] | 14.41 |  |  |  | 14.41 |  |  |
| NaOH (solid) |  |  |  |  |  |  | 1.70 |
| MEA |  |  |  |  |  |  | 2.80 |
| n-Butanol |  | 15.00 |  |  |  |  |  |
| i-$C_{13}$—O-(EO)$_6$[4] |  |  | 15.00 |  |  |  |  |
| n-Octylamine |  |  |  |  | 7.20 | 15.00 | 15.00 |
| $C_8/C_{18}$—N(EO)$_{20}$[5] | 7.20 |  | 15.00 |  |  |  |  |
| N-Methylpyrrolidone | 16.81 | 12.00 | 12.00 | 12.00 | 16.81 | 12.00 | 12.00 |
| Solvesso ® 200 | 7.20 | 6.00 | 6.00 | 6.00 | 7.20 | 6.00 | 6.00 |

TABLE 1-continued

Examples of formulations which do not give microemulsions (Comparative Examples)

|  | 1 | 2 | 3 | 4 | 5 | 6 | 7 |
|---|---|---|---|---|---|---|---|
| Acetic acid | 3.94 | 4.98 | 4.98 | 4.98 | 3.94 | 4.98 | 4.98 |
| Glycerol | 6.23 | 5.19 | 5.19 | 5.19 | 6.23 | 4.46 | 4.75 |

TABLE 2

Formulation Examples of microemulsions

|  | I | II | III | IV | V | VI | VII | VIII | IX | X | XI | XII | XIII | XIV |
|---|---|---|---|---|---|---|---|---|---|---|---|---|---|---|
| Glufosinate-ammonium | 9.98 | 9.60 | 10.37 | 10.58 | 11.97 | 10.86 | 10.51 | 13.17 | 10.08 | 10.07 |  | 10.10 | 9.98 | 9.98 |
| Glyphosate-isopropylammonium |  |  |  |  |  |  |  |  |  |  | 9.76 |  |  |  |
| Oxyfluorfen | 2.03 | 1.91 | 2.07 | 2.12 | 2.40 | 2.18 | 2.12 | 2.62 | 2.04 | 2.01 | 2.50 | 2.03 |  |  |
| Diclofop-methyl |  |  |  |  |  |  |  |  |  |  |  |  | 2.03 |  |
| Fenoxaprop-P-ethyl |  |  |  |  |  |  |  |  |  |  |  |  |  | 2.03 |
| $[\text{i-}C_{13}\text{—O-(EO)}_{10}]_n - PO_{4-n}H_{3-n}$ [1] | 19.95 |  |  |  |  | 21.72 |  |  | 16.58 | 17.15 | 19.62 | 20.27 | 19.95 | 19.95 |
| $[\text{i-}C_{13}\text{—O-(EO)}_{20}]_n - PO_{4-n}H_{3-n}$ [6] |  | 28.88 |  |  |  |  |  |  |  |  |  |  |  |  |
| $[C_{12}/C_{18}\text{—O-(EO)}_{10}]_n - PO_{4-n}H_{3-n}$ [2] |  |  | 20.88 |  |  |  | 18.46 |  |  |  |  |  |  |  |
| $[C_6H_5\text{—O-(EO)}_4]_n - PO_{4-n}H_{3-n}$ [7] |  |  |  |  |  |  |  | 13.24 |  |  |  |  |  |  |
| $[NP\text{—O-(EO)}_9]_n - PO_{4-n}H_{3-n}$ [8] |  |  |  | 21.14 |  |  |  |  |  |  |  |  |  |  |
| $[(\text{Tri-Sty-})\text{Phe-O-(EO)}_{16}]_n - PO_{4-n}H_{3-n}$ [9] |  |  |  |  | 14.37 |  |  |  |  |  |  |  |  |  |
| $C_{12}/C_{14}\text{—O-(EO)}_2\text{-SO}_3\text{—Na}^+$ [10] |  |  |  |  |  |  |  |  |  | 7.78 |  |  |  |  |
| $\text{i-}C_{13}\text{—O-(EO)}_7\text{-CH}_2CO_2H$ [11] |  |  |  |  |  |  |  |  |  |  | 7.15 |  |  |  |
| NaOH (solid) |  |  |  |  |  |  |  |  |  |  | 0.02 |  |  |  |
| n-Octylamine | 14.97 | 9.62 | 13.51 | 10.61 | 7.25 |  |  |  | 11.40 | 11.44 | 15.02 | 15.57 | 14.97 | 14.97 |
| n-Decylamine |  |  |  |  |  | 10.85 |  |  |  |  |  |  |  |  |
| $C_8/C_{18}\text{—N(EO)}_2$ [12] |  |  |  |  |  |  | 18.42 |  |  |  |  |  |  |  |
| $C_7/C_{17}\text{—CON(EO)}_2$ [13] |  |  |  |  |  |  |  | 7.88 |  |  |  |  |  |  |
| N-Methylpyrrolidone | 11.96 | 11.58 | 12.47 | 13.74 | 16.85 | 13.04 | 12.64 | 15.78 | 12.13 | 12.13 | 15.62 |  | 11.96 | 11.96 |
| Dowanol ® PM |  |  |  |  |  |  |  |  |  |  |  | 12.13 |  |  |
| Solvesso ® 200 | 6.08 | 5.73 | 6.22 | 6.37 | 7.20 | 6.53 | 6.36 | 7.87 | 6.12 | 6.04 | 7.51 | 6.09 | 6.08 | 6.08 |
| Acetic acid | 4.99 | 3.86 | 3.65 | 3.68 | 3.97 | 2.19 |  |  | 3.61 | 3.43 |  | 3.48 | 4.99 | 4.99 |
| Glycerol | 5.19 | 4.98 | 5.31 | 5.49 | 6.23 | 5.65 | 5.45 | 6.81 | 4.37 | 5.31 | 6.26 | 5.24 | 5.19 | 5.19 |

TABLE 3

Formulation Examples of single-phase aqueous solutions

| Components excluding water | Example 1 | Example 2 |
|---|---|---|
| Glufosinate-ammonium | 14.2 | 14.2 |
| $[\text{i-}C_{13}\text{—O-(EO)}_{10}]_n - PO_{4-n}H_{3-n}$ [1] | 20 | 20 |
| n-Octylamine | 15 | 15 |
| N-Methylpyrrolidone | 10 | 10 |
| Acetic acid | 5 | 5 |
| Glycerol | 5 | 5 |

USE EXAMPLE

Seeds or rhizome pieces of monocotyledonous and dicotyledonous weeds are placed in sandy loam soil in cardboard pots, covered with soil and cultivated in a greenhouse under good growth conditions. Three weeks after seeding, the test plants are treated in the three-leaf stage with the formulations and dosages according to Table 4 with an application rate of 300 l of water/ha. After the test plants have remained in the greenhouse for 28 days under optimum growth conditions, the effect of the preparations is scored visually by comparison with untreated controls. The results are summarized in Table 4.

TABLE 4

Biological results for herbicidal activity

| Formulation | Active compounds/ dose (a.i./ha) | Effect[c] | Harmful plant |
|---|---|---|---|
| Macro emulsion[a] | 450 g Glufosinate- ammonium + 90 g Oxyfluorfen | 70 | *Hordeum vulgaris* |
| Macro emulsion[a] |  | 96.5 | *Brassica napus* |
| Macro emulsion[a] |  | 55 | *Lolium multiflorum* |
| Macro emulsion[a] |  | 55 | *Stellaria medica* |
| Micro emulsion I[b] | 450 g Glufosinate- ammonium + 90 g Oxyfluorfen | 75 | *Hordeum vulgaris* |
| Micro emulsion I[b] | 450 g Glufosinate- ammonium + 90 g Oxyfluorfen | 98 | *Brassica napus* |
| Micro emulsion I[b] | 450 g Glufosinate- ammonium + 90 g Oxyfluorfen | 65 | *Lolium multiflorum* |
| Micro emulsion I[b] | 450 g Glufosinate- ammonium + 90 g Oxyfluorfen | 60 | *Stellaria media* |

[a] Formulation according to DE-A-19501986
[b] Microemulsion from Table 2
[c] Herbicidal effect in % after 28 days Abbreviations and footnotes for Tables, 1, 2, 3 and 4:

n in the formulae n=0–3, i.e. it is in each case a mixture of the phosphoric esters where n=1, 2 and 3, the acidic proportions where n=1 and 2 being essential;

numbers all percentages are percentages in percent by weight based on the weight of the formulation (=100 percent by weight); the remainder to 100 percent by weight is the percentage of water i-$C_{13}$-=isotridecyl $C_8/C_{18}$- or $C_{12}/C_{18}$- or $C_{12}/C_{14}$- are mixtures of fatty alkyl radicals having chain-lengths in the range of the chain-lengths given in C-atoms (Tri-Sty-)Phe-=tristyrylphenyl- EO "ethylene oxide", i.e. a group of the formula —$CH_2$—$CH_2$—O-(ethyleneoxy) or, if terminal, —$CH_2$—$CH_2$—O—H (hydroxyethyl)

TEA=triethanolamine

MEA=monoethanolamine

NP-=nonylphenyl

Explanations of the index numbers 1) to 13)):

1) phosphated ethoxylated isotridecyl alcohol (specifically Rhodafac RS 710®, (Rhone-Poulenc))
2) phosphated ethoxylated fatty alcohol (specifically Crafol AP 240®, Henkel)
3) phosphated ethoxylated tristyrylphenol, neutralized with TEA (specifically Soprophor FL®, Rhone-Poulenc); not according to the invention, because non-acidic;
4) ethoxylated isotridecyl alcohol (specifically Genapol X-060®, Clariant)
5) coconut fatty amine ethoxylate (specifically Genamin C-200®, Clariant); no cosurfactant in the context of the invention; forms aggregates (micelles);
6) phosphated ethoxylated isotridecyl alcohol (specifically Servoxyl VPDZ 20/100®, Hüls)
7) phosphated ethoxylated phenol having the following percentages in the mixture: 7.5–8.5% by weight n=0, 1–10% by weight $C_6H_5$—O—$(EO)_4$H, 80–90% by weight n=1 and approximately 2% by weight n=2
8) phosphated ethoxylated nonylphenol (specifically Rhodafac PA/19®, Rhone-Poulenc)
9) phosphated ethoxylated tristyrylphenol (specifically Soprophor 3D33® (Rhone-Poulenc))
10) fatty alcohol diethylene glycol ether sulfate (specifically Genapol LRO®, Clariant)
11) 2-(isotridecyloxypolyethyleneoxy)ethyl carboxymethyl ether (specifically marlowet 4538®, hüls)
12) coconut fatty amine ethoxylate (specifically Genamin C-020®, clariant)
13) fatty amide ethoxylate (specifically comperlan Ls®, henkel)

What is claimed is:

1. A liquid formulation for active compounds comprising
(a) one or more water-soluble active compounds (component (a));
(b) optionally one or more water-insoluble active compounds (component (b));
(c) optionally organic solvents;
(d) a surfactant system comprising one or more basic cosurfactants and one or more acidic surfactants, wherein the basic cosurfactant or cosurfactants are more soluble in an oil phase than in water and do not form micellar structures in water, and wherein the acidic surfactant or surfactants are acidic phosphoric esters; and
(e) water.

2. The formulation as claimed in claim 1, which comprises as water-soluble active compounds one or more compounds of the formula (1) or salts thereof,

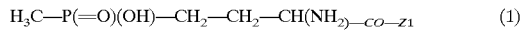

in which $Z_1$ is a radical of the formula —OM, —NHCH$(CH_3)$CONHCH$(CH_3)CO_2$M or —NHCH$(CH_3)$CONHCH$[CH_2CH(CH_3)_2]CO_2$M and M is H or a salt-forming cation, or one or more compounds of the formula (2) or salts thereof,

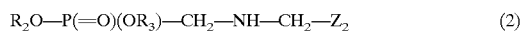

in which $Z_2$ is a radical of the formula CN or $CO_2R_1$, in which $R_1$ is Q or a salt-forming cation and Q is H, alkyl, alkenyl, alkoxyalkyl, or $C_6$–$C_{10}$-aryl, which is unsubstituted or substituted, and $R_2$, $R_3$ in each case independently of one another are H, alkyl, $C_6$–$C_{10}$-aryl which is unsubstituted or substituted or biphenyl or a salt-forming cation, or one or more compounds of the formula (3),

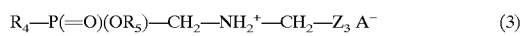

in which $Z_3$ is a radical CN or $CO_2Q'$ in which Q' is H, alkyl, alkenyl, alkoxyalkyl or $C_6$–$C_{10}$-aryl which is unsubstituted or substituted, and $R_4$ and $R_5$ are each H, alkyl or $C_6$–$C_{10}$-aryl which is unsubstituted or substituted, and A is a salt-forming anion, or mixtures of two or more of the above-defined compounds.

3. The formulation as claimed in claim 1, which comprises as water-insoluble active compounds compounds selected from the group of the diphenyl ether herbicides.

4. The formulation as claimed in claim 1, which comprises
(a) 1 to 50% by weight of active compounds of component (a),
(b) 0 to 70% by weight of active compounds of component (b),
(c) 0 to 60% by weight of organic solvents,
(d) 3 to 70% by weight of component mixture (d),
(e) 0 to 20% by weight of other anionogenic surfactants,
(f) 0 to 20% by weight of customary formulation auxiliaries, and
(g) 0.1 to 60% by weight of water.

5. The formulation as claimed in claim 1, wherein the formulations are microemulsions comprising
(a) 5 to 20% by weight of active compound of component (a),
(b) 1 to 10% by weight of active compound of component (b),
(c1) 5 to 30% by weight of organic solvents which form one phase with the active component (b),
(c2) 0 to 30% by weight of water-soluble organic solvents,
(d) 10 to 40% by weight of the component mixture (d), (e) 0 to 20% by weight of other anionogenic surfactants, (f) 0 to 20% by weight of customary formulation auxiliaries and (g) 10 to 40% by weight of water.

6. The formulation as claimed in claim 1, wherein the formulation is an aqueous single-phase solution of active compounds of component (a) comprising (a) 1 to 50% by weight of active compounds of component (a), (d) 3 to 70% by weight of component mixture (d), (c) 0 to 40% by weight of organic solvents which can be admixed without phase separation, (e) 0 to 20% by weight of other anionogenic surfactants, (f) 0 to 20% by weight of customary formulation auxiliaries and (g) 10 to 40% by weight of water.

7. The formulation as claimed in claim 1, wherein the water-soluble active compound is glufosinate-ammonium and the surfactant system is octylamine and phosphated ethoxylated isotridecyl alcohol.

8. The liquid formulation of claim 1, wherein the surfactant or surfactants from the group of acidic phosphoric esters are acid moieties esterified with one or more alcohol moieties selected from the group consisting of (a2), (b2), (c2), and (d2), wherein (a2) is an alkanol having 1 to 22 carbon atoms, or an unsubstituted or substituted cycloalkanol having 5 to 12 carbon atoms;

(b2) is an oxalkylated alkanol having up to 24 carbon atoms in the alkyl moiety and 1 to 150 alkyleneoxy units in the alkyleneoxy or polyalkyleneoxy moiety;

(c2) is a phenol or oxalkylated phenol, wherein the phenyl radical is unsubstituted, substituted by 1 to 3 alkyl radicals having 4 to 12 carbon atoms, or substituted by 1 to 3 aryl or arylalkyl radicals having 6 to 12 carbon atoms, and wherein the oxalkylated phenol contains 1 to 150 alkyleneoxy units in the alkyleneony or polyalkyleneoxy moiety; and (d2) is an oxalkylated alkylamine.

9. The liquid formulation of claim 1 wherein the acidic phosphoric ester surfactant or surfactants are selected from the group consisting of phosphated ethoxylated long-chain alcohols or fatty alcohols having 10 to 18 carbon atoms in the alkyl moiety and 1 to 30 ethyleneoxy units in the polyethyleneoxy moiety; phosphated ethoxylated phenols or alkylphenols having 4 to 12 carbon atoms in the alkyl moiety and 1 to 30 ethyleneoxy units in the polyethyleneoxy moiety; and phosphated ethoxylated tristyrylphenols having 1 to 150 ethyleneoxy units in the polyethyleneoxy moiety.

10. The liquid formulation of claim 1 wherein the basic cosurfactant or cosurfactants are selected from the group consisting of (a1), (b1), (c1), (d1), and (e1), wherein (a1) is an N-alkylamine, or an unsubstituted or substituted cycloalkylamine;

(b1) is an oxalkylated N-alkylamine;

(c1) is an alkylaminepolypropyleneamine;

(d1) is an oxalkylated amide or oxalkylated N-substituted amide; and (e1) is an alkylamidopropylamine.

11. A liquid formulation which comprises:

(a) one or more pharmaceutically insecticidally, fungicidally or herbicidally active compounds that are water-soluble;

(b) optionally, one or more pharmaceutically, insecticidally, fungicidally or herbicidally active compounds that are water-insoluble;

(c) optionally, an organic solvent;

(d) a surfactant system which comprises a mixture of one or more basic cosurfactants selected from the group consisting of N-alkylamines or unsubstituted or substituted cycloalkylamines having 5 to 22 carbon atoms, oxalkylated products of N-alkylamines, alkylaminepolypropyleneamines, oxalkylated products or amides or N-substituted amides, alkylamidopropylamines, and one or more acid phosphoric acid ester surfactants in which the esterified acid radicals are esterified with one or more compounds selected from the group consisting of alkanols having 1 to 22 carbon atoms, or unsubstituted or substituted cycloaklanols having 5 to 12 carbon atoms, oxalkylated alkanols having up to 24 carbon atoms in the alkyl radical and 1 to 15 alkyleneoxy units in the alkyleneoxy or polyalkyleneoxy moiety and phenol or oxalkylated phenol, where the phenyl radical is in each case unsubstituted or substituted by one, two or three alkyl radicals having in each case 4 to 12 carbon atoms or by one, two or three aryl or arylalkyl radicals having 6 to 12 carbon atoms and having, in the oxalkylated case, 1 to 150 alkyleneoxy units in the alkyleneoxy or polyalkyleneoxy moiety, and oxalkylated alkylamines;

and water, wherein said formulation is an aqueous single-phase solution or a microemulsion, which is thermodynamically stable.

12. The liquid formulation according to claim 11, wherein the water-soluble active compound is a herbicide selected from the group of the diphenyl ethers, carbamates, thiocarbamates, halocetanilides, phenoxyphenoxycarboxylic acid derivatives and heteraryloxyphenoxyalkanecarboxylic acid derivatives, and the water-insoluble active compound is a herbicide selected from the group consisting of cyclohexanedione derivatives, imidazoleinones, pyrimidyloxypyridinecarboxylic acid derivatives, pyrimidyloxybenzoic acid derivatives, sulfonylureas, triazoleopyrimidinesulfonamide derivatives and S-(N-aryl-N-alkylcarbamoylmethyl)dithiophosphoric esters.

13. The formulation as claimed in claim 11, wherein the water-soluble active compound is glufosinate-ammonium and the surfactant system is octylamine and phosphated ethoxylated isotridecyl alcohol.

14. A process for preparing a formulation as defined in claim 1, which comprises mixing the components (a) to (d) and, if appropriate, other components which are meant to be part of the formulation, with water.

15. A process as claimed in claim 14, wherein the formulation is a microemulsion.

16. A method for controlling undesirable plant growth, which comprises applying an effective amount of a formulation as claimed in claim 2 onto the plants, parts of plants or the area under cultivation.

* * * * *